(12) United States Patent
Zhang (10) Patent No.: US 11,501,178 B2
(45) Date of Patent: Nov. 15, 2022

(54) DATA PROCESSING METHOD, MEDICAL TERM PROCESSING SYSTEM AND MEDICAL DIAGNOSTIC SYSTEM

(71) Applicant: BOE TECHNOLOGY GROUP CO., LTD., Beijing (CN)

(72) Inventor: Zhenzhong Zhang, Beijing (CN)

(73) Assignee: BEIJING BOE TECHNOLOGY DEVELOPMENT CO., LTD., Beijing (CN)

( * ) Notice: Subject to any disclaimer, the term of this patent is extended or adjusted under 35 U.S.C. 154(b) by 1252 days.

(21) Appl. No.: 15/953,234

(22) Filed: Apr. 13, 2018

(65) Prior Publication Data

US 2019/0034810 A1     Jan. 31, 2019

(30) Foreign Application Priority Data

Jul. 31, 2017 (CN) .......................... 201710642037.8

(51) Int. Cl.
*G06N 5/02* (2006.01)
*G16H 15/00* (2018.01)
(Continued)

(52) U.S. Cl.
CPC ......... *G06N 5/022* (2013.01); *G06F 16/3344* (2019.01); *G06F 40/30* (2020.01);
(Continued)

(58) Field of Classification Search
CPC ........ G06N 20/00; G06N 20/10; G06N 20/20; G06N 5/02; G06N 5/022; G06N 5/025;
(Continued)

(56) References Cited

U.S. PATENT DOCUMENTS

2003/0167245 A1    9/2003 Murata
2012/0232884 A1*   9/2012 Nasukawa .............. G06F 40/42
                                                                    704/8
(Continued)

FOREIGN PATENT DOCUMENTS

CN    103838712 A    6/2014
CN    104636496 A    5/2015
CN    106933806 A    7/2017

OTHER PUBLICATIONS

Office Action received for Chinese Patent Application No. 201710642037.8, dated May 6, 2020, 13 pages (5 pages of English Translation and 8 pages of Office Action).

*Primary Examiner* — Shane D Woolwine
(74) *Attorney, Agent, or Firm* — Womble Bond Dickinson (US) LLP (57) ABSTRACT

The present disclosure relates to a data processing method, a medical term processing system, a medical diagnostic system, a medical intelligent triage apparatus and a computer readable storage medium. The method comprises: acquiring statement information inputted by a user; dividing the statement information into a plurality of information segments by means of a predetermined algorithm, the plurality of information segments comprising a first information segment; establishing a Gaussian distribution of each of the information segments; calculating the similarity between the first information segment and words in a database by means of a similarity model; and obtaining, from words in the database, at least one second information segment for describing the first information segment based on the calculated similarity. The present disclosure can provide professional terms, such as medical terms, corresponding to colloquial expressions, to facilitate users' diagnosis and treatment.

16 Claims, 3 Drawing Sheets

(51) Int. Cl.
  *G06F 40/30* (2020.01)
  *G06F 16/33* (2019.01)
  *G16H 70/20* (2018.01)
  *G06F 40/216* (2020.01)
  *G16H 50/20* (2018.01)

(52) U.S. Cl.
  CPC ........... *G16H 15/00* (2018.01); *G06F 40/216* (2020.01); *G16H 50/20* (2018.01); *G16H 70/20* (2018.01)

(58) Field of Classification Search
  CPC .... G06N 5/027; G06N 5/047; G06F 16/3344; G06F 40/30; G06F 40/216; G16H 15/00; G16H 50/20; G16H 70/20
  See application file for complete search history.

(56) References Cited

U.S. PATENT DOCUMENTS

| 2016/0110343 | A1* | 4/2016 | Kumar Rangarajan Sridhar ........ G06F 40/216 704/9 |
| 2016/0283491 | A1* | 9/2016 | Lu ....................... G06F 16/3322 |
| 2017/0270409 | A1* | 9/2017 | Trischler ................ G06F 40/30 |
| 2019/0295719 | A1* | 9/2019 | Van De Steen ........ G16H 10/60 |

\* cited by examiner

DATA PROCESSING METHOD, MEDICAL TERM PROCESSING SYSTEM AND MEDICAL DIAGNOSTIC SYSTEM

RELATED APPLICATIONS

The present application claims the benefit of Chinese Patent Application No. 201710642037.8, filed on Jul. 31, 2017, the entire disclosure of which is incorporated herein by reference.

TECHNICAL FIELD

The present invention relates to the field of medical technology, and more particular to a data processing method, a medical term processing system and a medical diagnostic system.

BACKGROUND ART

A huge number of people go to see doctors each year in China, so that hospitals always operate under an excessive burden, which leaves an impression of low efficiency in medical service. If an artificial intelligence system can be used to improve the efficiency and automation degree of healthcare service, such a problem can be alleviated to some extent. However, the application of an artificial intelligence system to improve healthcare efficiency may usually come across a severe problem: due to lack of medical knowledge and language complexity, patients tend to make mistakes when describing their symptoms (such as descriptive errors, misuse of words, or purposeful or unintentional omission), so pure matching of written symptoms with medical terms may give rise to misdiagnosis. Here is a simple example. Medical literature often use the term "nasal obstruction" to describe a symptom of cold, whereas patients in reality often say "my nose is stuffed up" and "my nose is bunged up". From this example, we can see a big difference between medical terms and colloquial expressions. Misdiagnosis will result from simple morphological matching of words or characters. Thus, if a relevant medical term can be provided according to patient's information, medical service efficiency can be greatly enhanced and misdiagnosis can be prevented.

SUMMARY

According to an aspect of the present disclosure, there is provided a data processing method, comprising: acquiring statement information inputted by a user; dividing the statement information into a plurality of information segments by means of a predetermined algorithm, the plurality of information segments comprising a first information segment; establishing a Gaussian distribution of each of the information segments; calculating the similarity between the first information segment and words in a database by means of a similarity model; and obtaining, from words in the database, at least one second information segment for describing the first information segment based on the calculated similarity.

In an embodiment, the dividing the statement information into a plurality of information segments by means of a predetermined algorithm comprises: dividing the statement information into a plurality of information segments according to part of speech by means of a natural language processing algorithm.

In an embodiment, the establishing a Gaussian distribution of each of the information segments comprises: expressing an initial Gaussian distribution of each of the information segments by a random initial vector and a random initial matrix, wherein the initial vector and the initial matrix are respectively an expected value vector and a covariance matrix of the initial Gaussian distribution; solving a covariance and an expected value of the Gaussian distribution of each of the information segments by minimizing a target function; and establishing the Gaussian distribution of each of the information segments based on the calculated covariance and expected value.

In an embodiment, the solving a covariance and an expected value of the Gaussian distribution of each of the information segments by minimizing a target function comprises: iteratively solving a target function by means of a random gradient descent algorithm so as to calculate a covariance and an expected value of the Gaussian distribution of each of the information segments, wherein the target function is expressed as follows:

$$L(w, c_p, c_n) = \max(0, 1 - S_1(w, c_p) + S_1(w, c_n));$$

Wherein w is the information of an information segment, $c_p$ is an information segment in the context of w in a statement, $c_n$ is a word not in the context of w in a statement, the function $S_1(w, c_n)$ is a similarity function between w and $c_n$, $S_1(w, c_p)$ is a similarity function between w and $c_p$, and max( ) is a maximum function.

In an embodiment, the Gaussian distribution is a multi-dimensional Gaussian distribution that is expressed as $N(u_w, \Sigma_w)$, wherein $\Sigma_w$ is a covariance of the Gaussian distribution of the information segment w, $u_w$ is an expectation of the Gaussian distribution of the information segment w.

In an embodiment, the iteratively solving a target function by means of a random gradient descent algorithm comprises iterating the following processes until a predetermined condition is met:

solving a partial derivative of the target function with respect to an expected value vector and a covariance matrix:

$$\frac{\partial L}{\partial u_{w1}} = -\sum\nolimits_{w1}^{-1}(u_{w1} - w_2)$$

$$\frac{\partial L}{\partial \Sigma_{w1}} = \frac{1}{2}\left(\sum\nolimits_{w1}^{-1}\sum\nolimits_{w2}\sum\nolimits_{w1}^{-1} + \left(\sum\nolimits_{w1}^{-1}(u_{w1} - u_{w2})\right)\left(\sum\nolimits_{w1}^{-1}(u_{w1} - u_{w2})\right)^T - \sum\nolimits_{w1}^{-1}\right)$$

wherein $\Sigma$ is a covariance of the Gaussian distribution of an information segment, u is an expectation of the Gaussian distribution of an information segment, and $w_1$ and $w_2$ are two information segments;

updating the expected value vector and the covariance matrix according to the partial derivatives.

In an embodiment, the calculating the similarity between the first information segment and words in a database by means of a similarity model comprises: establishing a similarity model according to the calculated first information segment, and the covariance and the expected value of the Gaussian distribution of the words in the database; and calculating the similarity between the first information segment and the words in the database.

In an embodiment, the similarity model is expressed as $$S(w_1, w_2) = \int N\left(x; u_{w_1}, \sum_{w_1}\right) \log \frac{N\left(x; u_{w_2}, \sum_{w_2}\right)}{N\left(x; u_{w_1}, \sum_{w_1}\right)} dx$$

$$= \frac{1}{2}\left\{ tr\left(\sum_{w_1}^{-1} \sum_{w_2}\right) + (u_{w_1} - u_{w_2})^T \sum_{w_1}^{-1} (u_{w_1} - u_{w_2}) - \log\frac{\det(\sum_{w_2})}{\det(\sum_{w_1})} - d \right\}$$

wherein, d is a constant, u is the expectation of the Gaussian distribution of an information segment, Σ is the covariance of the Gaussian distribution of an information segment, $w_1$ and $w_2$ are two information segments, and N is the multi-dimensional Gaussian distribution in the form of matrix of an information segment.

In an embodiment, the obtaining at least one second information segment for describing the first information segment comprises: sorting the words in the database according to the similarity between the words in the database and the first information segment so as to obtain a predetermined number of words having highest similarity; and using the predetermined number of words as the second information segment.

In an embodiment, the method is applied in a diagnostic system, and the database comprises at least one of medical literature, medical knowledge base and electronic medical records.

According to another aspect of the present disclosure, there is provided a medical term processing system using the above method, which is to be applied in a medical information processing system, the medical term processing system comprises: a database configured to store information in relation to medical term; a data processor configured to divide statement information inputted by a user into a plurality of information segments, the plurality of information segments comprising a first information segment; a Gaussian embedder configured to establish a Gaussian distribution of each of information segments; a similarity calculator configured to calculate the similarity between the first information segment and words in the database by means of a similarity model, the words in the database comprising the plurality of information segments; and an output module configured to obtain at least one second information segment for describing the first information segment according to the calculated result of the similarity calculator.

In an embodiment, the data processor is configured to divide the statement information into a plurality of information segments according to part of speech by means of a natural language processing algorithm.

In an embodiment, the Gaussian embedder is configured to express an initial Gaussian distribution of each of the information segments by a random initial vector and a random initial matrix, wherein the initial vector and the initial matrix are respectively an expected value vector and a covariance matrix of the initial Gaussian distribution, and the Gaussian embedder is configured to solve a covariance and an expected value of the Gaussian distribution of each of the information segments by minimizing a target function, and establish the Gaussian distribution of each of the information segments based on the calculated covariance and expected value.

In an embodiment, the similarity calculator is configured to establish a similarity model according to the calculated first information segment and the covariance and the expected value of the Gaussian distribution of the words in the database; calculate the similarity between the first information segment and the words in the database; and sort the words in the database according to the similarity between the words in the database and the first information segment.

In an embodiment, the output module is configured to output a predetermined number of words as the second information segment according to the order of the words in the database.

In an embodiment, the solving a covariance and an expected value of the Gaussian distribution of each of the information segments by minimizing a target function comprises: iteratively solving a target function by means of a random gradient descent algorithm so as to calculate a covariance and an expected value of the Gaussian distribution of each of the information segments, wherein the target function is expressed as follows:

$$L(w, c_p, c_n) = \max(0, 1 - S_1(w, c_p) + S_1(w, c_n));$$

Wherein w is information of an information segment, $c_p$ is an information segment in the context of w in a statement, $c_n$ is a word not in the context of w in a statement, the function $S_1(w, c_n)$ is a similarity function between w and $c_n$, $S_1(w, c_p)$ is a similarity function between w and $c_p$, and max( ) is a maximum function.

In an embodiment, the iteratively solving a target function by means of a random gradient descent algorithm comprises iterating the following processes until a predetermined condition is met:

solving a partial derivative of the target function with respect to an expected value vector and a covariance matrix:

$$\frac{\partial L}{\partial u_{w1}} = -\sum_{w1}^{-1}(u_{w1} - w_2)$$

$$\frac{\partial L}{\partial \Sigma_{w1}} =$$
$$\frac{1}{2}\left(\sum_{w1}^{-1}\sum_{w2}\sum_{w1}^{-1} + \left(\sum_{w1}^{-1}(u_{w1} - u_{w2})\right)\left(\sum_{w1}^{-1}(u_{w1} - u_{w2})\right)^T - \sum_{w1}^{-1}\right)$$

wherein Σ is a covariance of the Gaussian distribution of an information segment, u is an expectation of the Gaussian distribution of an information segment, and $w_1$ and $w_2$ are two information segments;

updating the expected value vector and the covariance matrix according to the partial derivatives.

In an embodiment, the similarity model is expressed as $$S(w_1, w_2) = \int N\left(x; u_{w_1}, \sum_{w_1}\right) \log \frac{N\left(x; u_{w_2}, \sum_{w_2}\right)}{N\left(x; u_{w_1}, \sum_{w_1}\right)} dx$$

$$= \frac{1}{2}\left\{ tr\left(\sum_{w_1}^{-1} \sum_{w_2}\right) + (u_{w_1} - u_{w_2})^T \sum_{w_1}^{-1} (u_{w_1} - u_{w_2}) - \log\frac{\det(\sum_{w_2})}{\det(\sum_{w_1})} - d \right\}$$

wherein, d is a constant, u is the expectation, Σ is the covariance, $w_1$ and $w_2$ are two information segments.

According to another aspect of the present disclosure, there is provided a medical diagnostic system comprising a medical term processing system as stated above and further comprising: a receiving apparatus for receiving the statement information on disease features inputted by a user. The medical diagnostic system divides the statement information into a plurality of information segments by means of the medical term processing system, the plurality of information segments comprising a first information segment, and outputs at least one second information segment for describing the first information segment.

According to another aspect of the present disclosure, there is provided a medical intelligent triage apparatus, comprising: one or more processors; and a memory storing computer executable instructions configured to perform the method as stated above when executed by the one or more processors.

According to another aspect of the present disclosure, there is provided a computer readable storage medium, comprising computer executable instructions that causes one or more processors to perform the method as stated above when executed by the one or more processors.

Some embodiments of the present disclosure can realize at least one of the following advantageous effects and/or other advantageous effects: some embodiments can conveniently output professional terms that are close to the inputted colloquial expressions, so as to eliminate the differences between professional terms and colloquial expressions for users' easy use. For instance, some embodiments can conveniently output medical terms that are close to the inputted colloquial expressions, so as to eliminate the differences between medical terms and colloquial expressions for users' easy use.

The Summary introduces some concepts of the present invention in a simplified form, which will be further described in the following Detailed Description. The Summary is intended neither to provide essential features or substantive features of the claimed subject matter, nor to limit the scope of protection of the subject matter. Furthermore, as described herein, other various features and advantages can also be incorporated into these technologies as required.

BRIEF DESCRIPTION OF DRAWINGS

To explain some embodiments of the present disclosure more clearly, the present disclosure provides the following drawings used for describing the embodiments. It should be realized that the following drawings are only related to some embodiments. Those skilled in the art can obtain other drawings according to these drawings without making inventive effort, and the other drawings also fall within the scope of the present invention.

DETAILED DESCRIPTION

To understand the objects, technical solutions and advantages of some embodiments more clearly, the embodiments will be described in detail with reference to the drawings and implementations. Those ordinarily skilled in the art shall understand that the embodiments described herein are only used to explain the present invention by way of examples, and not to impose limitations to the present invention.

Drawings included in the description and constituting a part of the description show some embodiments of the present disclosure, and are used, together with brief description of the present disclosure as stated above and detailed description of embodiments described later, to explain the principle of the present disclosure.

Some embodiments of the present disclosure will be described with reference to the drawings. However, it shall be understood that embodiments disclosed herein are merely examples of the present disclosure and can be implemented in many ways. Known and/or repeated functions and structures are not described in detail in order to prevent unnecessary or redundant details from making the present disclosure ambiguous. Thus, specific structural and functional details disclosed herein are not used for limitation, but as claim basis and representative basis to teach those skilled in the art to diversely use the present disclosure with any substantively suitable detailed structure.

The expressions, "in an embodiment", "in one embodiment", "in another embodiment", "in a further embodiment" or "in other embodiment", in the description all refer to one or more identical or different embodiments according to the present disclosure.

Some embodiments of the present disclosure will be explained in detail with reference to the drawings, wherein a data processing method is provided, the method expresses a professional term as a multi-dimensional Gaussian distribution via Gaussian embedding, and finds out a similar term through relative entropy between the multi-dimensional Gaussian distributions, so as to locate a professional term that is close to the inputted term quickly and accurately, and solve the problem of difference between professional terms and colloquial expressions. For instance, the professional terms can be medical terms, financial terms, commercial terms, etc., which will not be limited therein. It shall be noted that for easy description, the present description will only use medical terms as an example to explain some embodiments of the present invention. However, on the basis of the recitation of the description, those ordinarily skilled in the art can readily arrive at some embodiments of the present invention used for other professional terms, which will also fall within the scope of the present invention.

Figure 1:
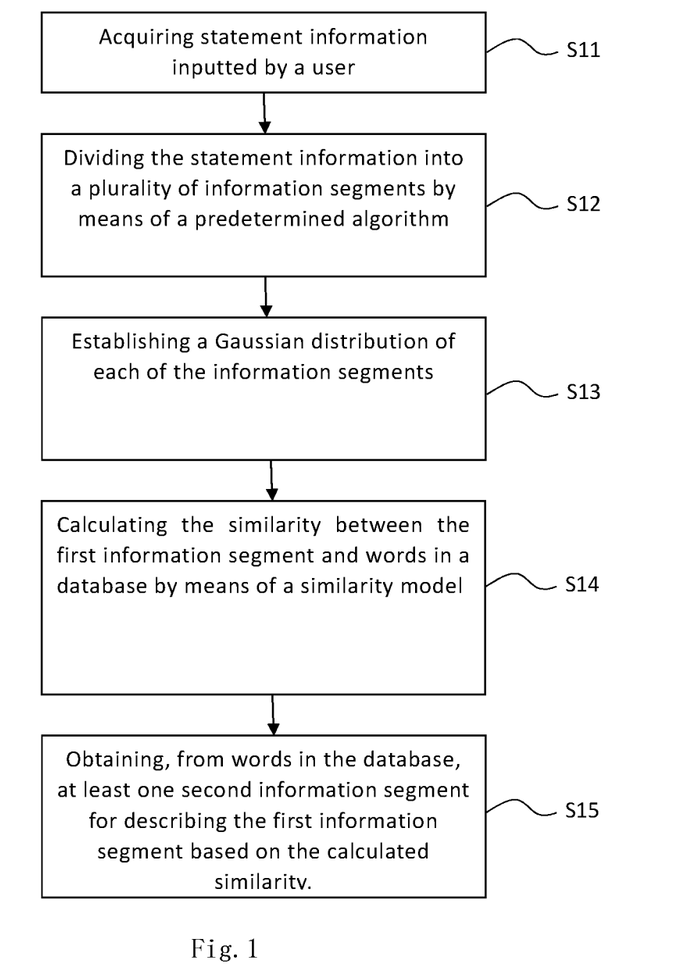
FIG. 1 is a flowchart showing the principle of a data processing method according to an embodiment of the present disclosure.

FIG. 1 shows a flowchart showing the principle of a data processing method according to an embodiment of the present disclosure. In an embodiment, the method can be used in a diagnostic system that provides medication recommendations or disease diagnosis according to the inputted symptoms. In some other embodiments, the method can be used in, e.g., automated teller machines, automated vending machines, or automated customer service systems, which will not be limited herein.

As shown in FIG. 1, the data processing method can comprise:

Step S11: acquiring statement information inputted by a user;

Step S12: dividing the statement information into a plurality of information segments by means of a predetermined algorithm, the plurality of information segments comprising a first information segment;

Step S13: establishing a Gaussian distribution of each of the information segments;

Step S14: calculating the similarity between the first information segment and words in a database by means of a similarity model, the words in the database comprising the plurality of information segments; and Step S15: obtaining, from words in the database, at least one second information segment for describing the first information segment based on the calculated similarity.

If the data processing method is used in a diagnostic system, a user, when inquiring a treatment, medication or other specific information in relation to a disease, can input relevant statement information into the diagnostic system, the statement information can be a sentence, or a phrase/word, such as hand numbness or a bunged-up nose. A user can input relevant statement information according to the symptoms. Then, the diagnostic system can acquire the statement information inputted by the user, and divide the acquired statement information into a plurality of information segments by means of a predetermined algorithm, the plurality of information segments comprising a first information segment. For instance, if the statement information inputted by a user is that "my nose is bunged up", the statement information can be divided into two information segments, "my" and "nose is bunged up", or three information segments, "my", "nose" and "bunged up", wherein "nose is bunged up" or "bunged up" can serve as the first information segment. In an embodiment, the acquired statement information can be divided into a plurality of information segments according to part of speech by means of a natural language processing algorithm.

In addition, after the statement information is divided into a plurality of information segments, a Gaussian distribution of each of the information segments can be established, namely, each of the information segments can be expressed as a Gaussian distribution. The similarity between the first information segment and words in a database can be calculated by means of a similarity model, and at least one second information segment for describing the first information segment can be obtained. Wherein the database can comprise medical terms, to be specific, it can comprise at least one of medical literature, medical knowledge base and electronic medical records. After a second information segment is acquired, a medical statement that is close to the inputted statement can be generated on the basis of the second information segment. The diagnostic system can also output corresponding information according to the generated second information segment or the generated medical statement.

Through the above configuration, a term that is close to the inputted statement can be obtained, for example, it can be obtained that the term that is close to "nose is bunged up" is "nasal obstruction", in such a way to quickly and accurately provide a medical term that is close to the inputted statement, and eliminate the differences between medical terms and colloquial expressions.

Figure 2:
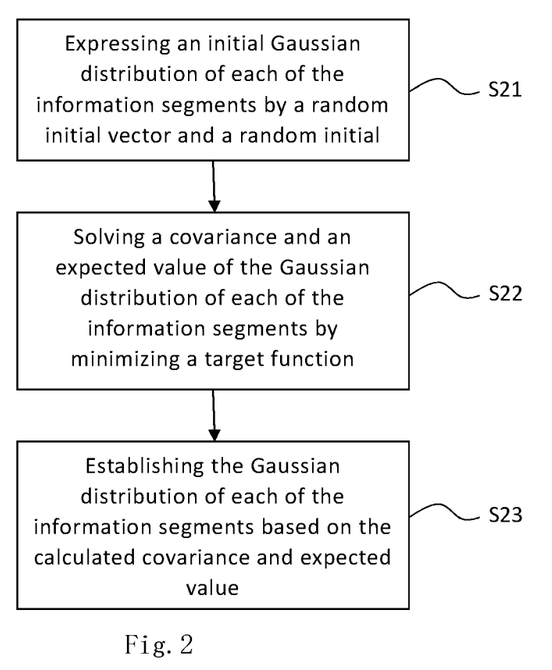
FIG. 2 is a process flowchart of establishing a Gaussian distribution of each of information segments according to an embodiment of the present disclosure.

FIG. 2 is a process flowchart of establishing a Gaussian distribution of each of information segments according to an embodiment of the present disclosure. As shown in FIG. 2, the method can comprise:

Step S21: expressing an initial Gaussian distribution of each of the information segments by a random initial vector and a random initial matrix, wherein the initial vector and the initial matrix are respectively an expected value vector and a covariance matrix of the initial Gaussian distribution;

Step S22: solving a covariance and an expected value of the Gaussian distribution of each of the information segments by minimizing a target function; and Step S23: establishing the Gaussian distribution based on the calculated covariance and expected value.

The steps of the method will be described in detail. Firstly, the use of the signs will be explained. Let w be an information segment, and $c(w)_i$ refers to the i-th information segment in the context of w. Each information segment w can be expressed as a multi-dimensional Gaussian distribution $N(u_w, \Sigma_w)$, wherein u and $\Sigma$ respectively indicates an expected value vector and a covariance matrix of the multi-dimensional Gaussian distribution corresponding to the information segment w. To simplify the model and calculation, $\Sigma$ can be set as a diagonal matrix. Thus, in order to obtain the Gaussian distribution corresponding to the information segment w, it is required to solve a covariance and an expected value of the Gaussian distribution of each of the information segments by minimizing a target function. In an embodiment, the expressing the Gaussian distribution of each of the information segments in the form of matrix comprises:

the Gaussian distribution is a multi-dimensional Gaussian distribution, and the multi-dimensional Gaussian distribution in the form of matrix is expressed as $N(u_w, \Sigma_w)$, wherein $\Sigma_w$ means that $\Sigma$ is a covariance matrix of the Gaussian distribution of the information segment w, and $u_w$ is an expected value vector of the Gaussian distribution of the information segment w.

In an embodiment, the solving a covariance and an expected value of the Gaussian distribution of each of the information segments by minimizing a target function can comprise: iteratively solving a target function by means of a random gradient descent algorithm so as to calculate a covariance and an expected value of the Gaussian distribution of each of the information segments, wherein the target function is expressed as follows:

$$L(w, c_p, c_n) = \max(0, 1 - S_1(w, c_p) + S_1(w, c_n));$$

Wherein w is the information segment for which the Gaussian distribution is to be found, $c_p$ is an information segment in the context of w in a statement, $c_n$ is a word not in the context of w in a statement, the function $S_1(w, c_n)$ is a similarity function between w and $c_n$, $S_1(w, c_p)$ is a similarity function between w and $c_p$, and max( ) is a maximum function.

The purpose of minimizing the target function is to make sure that the similarity between the information segment in the context of w and w is higher than at least the similarity between words not in the context of w and w.

In an embodiment, the iteratively solving a target function by means of a random gradient descent algorithm comprises iterating the following processes until a predetermined condition is met:

solving a partial derivative of the target function with respect to an expected value vector and a covariance matrix:

$$\frac{\partial L}{\partial u_{w1}} = -\sum\nolimits_{w1}^{-1}(u_{w1} - w_2)$$

$$\frac{\partial L}{\partial \Sigma_{w1}} =$$

$$\frac{1}{2}\left(\sum\nolimits_{w1}^{-1}\sum\nolimits_{w2}\sum\nolimits_{w1}^{-1} + \left(\sum\nolimits_{w1}^{-1}(u_{w1} - u_{w2})\right)\left(\sum\nolimits_{w1}^{-1}(u_{w1} - u_{w2})\right)^T - \sum\nolimits_{w1}^{-1}\right)$$

wherein $\Sigma$ is a covariance matrix of the Gaussian distribution of an information segment, u is an expected value vector of the Gaussian distribution of an information segment, and $w_1$ and $w_2$ are two information segments;

updating the expected value vector and the covariance matrix according to the partial derivatives.

In order to solve the expected value vector and the covariance matrix of the Gaussian distribution, the present disclosure also defines a similarity function, which is expressed as:

$$S_1(w_1, w_2) = \int N\left(x; u_{w_1}, \sum\nolimits_{w_1}\right) \log \frac{N\left(x; u_{w_2}, \sum\nolimits_{w_2}\right)}{N\left(x; u_{w_1}, \sum\nolimits_{w_1}\right)} dx$$

$$= \frac{1}{2}\left\{tr\left(\sum\nolimits_{w_1}^{-1}\sum\nolimits_{w_2}\right) + (u_{w_1} - u_{w_2})^T \sum\nolimits_{w_1}^{-1}(u_{w_1} - u_{w_2}) - \log \frac{\det(\sum\nolimits_{w_2})}{\det(\sum\nolimits_{w_1})} - d\right\}$$

Wherein tr( ) means solving a trace of a matrix, $\Sigma^{-1}$ means the inverse of a matrix, det means solving the value of a determinant, and d is a constant. On the basis of the above definitions and expressions, the present disclosure solves u and $\Sigma$ by means of a random gradient descent algorithm, and $w_1$ and $w_2$ are two information segments.

Figure 3:
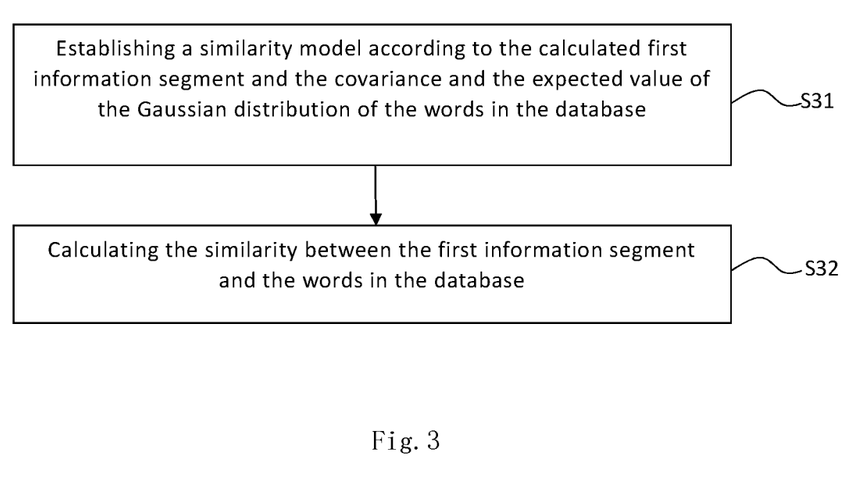
FIG. 3 is a process flowchart of calculating the similarity between a first information segment and words in the database by a similarity model according to an embodiment of the present disclosure.

By means of the similarity function, the target function of each information segment, as well as its expected value vector and covariance matrix when the target function is minimized, can be obtained, and therefore the Gaussian distribution of the corresponding information segment can be obtained, FIG. 3 is a process flowchart of calculating the similarity between a first information segment and words in a database by a similarity model according to an embodiment of the present disclosure. As shown in FIG. 3, the method can comprise:

Step S31: establishing a similarity model according to the calculated first information segment, and the covariance and the expected value of the Gaussian distribution of the words in the database; and Step S32: calculating the similarity between the first information segment and the words in the database.

In an embodiment, the similarity model is expressed as $$S(w_1, w_2) = \int N\left(x; u_{w_1}, \sum\nolimits_{w_1}\right) \log \frac{N\left(x; u_{w_2}, \sum\nolimits_{w_2}\right)}{N\left(x; u_{w_1}, \sum\nolimits_{w_1}\right)} dx$$

$$= \frac{1}{2}\left\{tr\left(\sum\nolimits_{w_1}^{-1}\sum\nolimits_{w_2}\right) + (u_{w_1} - u_{w_2})^T \sum\nolimits_{w_1}^{-1}(u_{w_1} - u_{w_2}) - \log \frac{\det(\sum\nolimits_{w_2})}{\det(\sum\nolimits_{w_1})} - d\right\}$$

wherein, d is a constant, u is the expected value vector, $\Sigma$ is the covariance matrix, and $w_1$ and $w_2$ are two information segments.

It can be understood that the similarity model $S(w_1,w_2)$ for calculating the similarity of the two information segments $w_1$ and $w_2$ can be the same as, or different from, the similarity function $S_1(w_1,w_2)$ for solving the Gaussian distribution of an information segment, because they represent the similarity of two information segments in different solving processes. In the solution of an embodiment where the two similarity functions are the same, the calculated similarity between the information segments is more precise. In the similarity model $S(w_1,w_2)$, the two information segments $w_1$ and $w_2$ used for comparing the similarities respectively represent the acquired information segment inputted by a user and the information segment in the database; and when solving the Gaussian distribution of an information segment, the two information segments $w_1$ and $w_2$ used for comparing the similarities respectively represent the information segment for which the Gaussian distribution is to be solved, and an information segment in the context of the information segment in a statement or an information segment not in the context of the information segment in a statement.

When acquiring the words close to the first information segment by the above configuration, the words can be outputted according to the similarity thereof.

Figure 4:
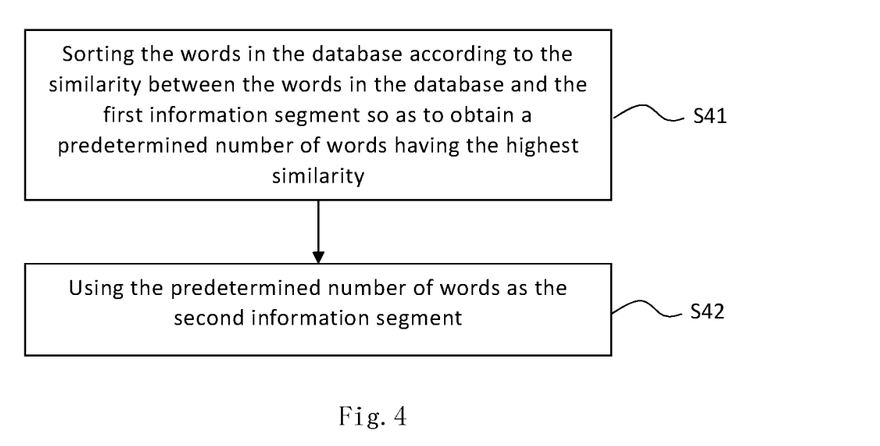
FIG. 4 is a flowchart showing the principle of acquiring at least one second information segment for describing the first information segment according to an embodiment of the present disclosure.

FIG. 4 is a flowchart showing the principle of acquiring at least one second information segment for describing the first information segment according to an embodiment of the present disclosure. As shown in FIG. 4, the method can comprise:

Step S41: sorting the words in the database according to the similarity between the words in the database and the first information segment so as to obtain a predetermined number of words having the highest similarity; and Step S42: using the predetermined number of words as the second information segment.

In the above embodiment, the number of close medical terms to be acquired, namely, the predetermined number, can be set beforehand, and the corresponding number of medical terms (words) can be outputted according to the predetermined number after obtaining the similarity between the first information segment and other words. Thus, at least one medical term that is close to the inputted statement can be acquired, which can help a user inquire information on a disease by using the medical term.

On this basis, the above embodiment can also further output information on, e.g., the corresponding department, treatment or medication of a disease according to the acquired medical term to provide a better user-friendly experience.

Figure 5:
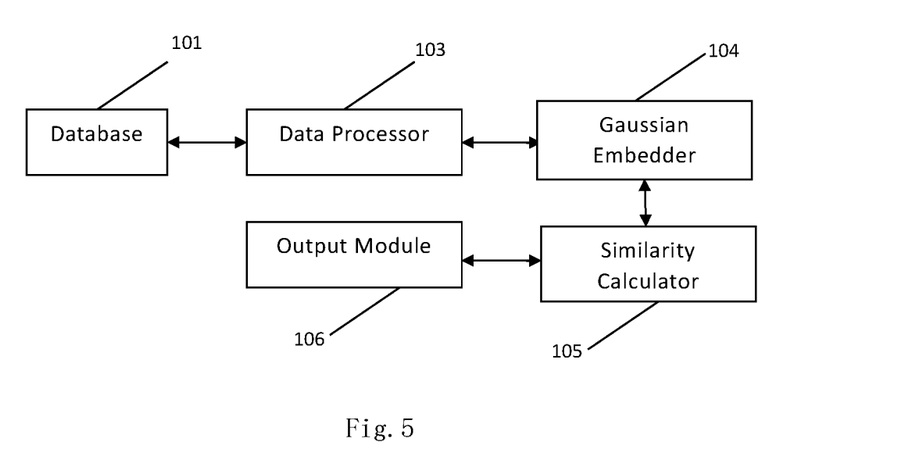
FIG. 5 is a structural block diagram of a medical term processing system according to an embodiment of the present disclosure.

According to another aspect of the present disclosure, there is provided a medical term processing system, which is applied in a medical information processing system, which can apply the above data processing method. FIG. 5 is a structural block diagram of the medical term processing system. As shown in FIG. 5, the medical term processing system can comprise:

a database 101 that can be configured to store medical terms, which can comprise, for example, at least one of medical literature, medical knowledge base and electronic medical records;

a data processor 103 that can be configured to divide received statement information into a plurality of information segments, the plurality of information segments comprising a first information segment;

a Gaussian embedder 104 that can be configured to receive information of the information segments outputted by the data processor 103 and establish a Gaussian distribution of each of the information segments;

a similarity calculator 105 that can be configured to calculate the similarity between the first information segment among the information segments and words in the database 101 by means of a similarity model; and an output module 106 that can be configured to obtain at least one second information segment for describing the first information segment according to the calculated result of the similarity calculator 105.

In an embodiment, when inquiring a disease-related treatment or medication, or other specific relevant information, a user can input relevant statement information into a diagnostic system, and the data processor 103 can acquire the inputted statement information. The inputted statement information can be a sentence or a phrase/word, such as hand numbness or a bunged-up nose. A user can input relevant statement information according to the symptoms. Then, the data processor 103 can directly detect the information inputted by a user, or acquire the statement information inputted by the user through communication with other receiving device, and divide the acquired statement information into a plurality of information segments by means of a predetermined algorithm, the plurality of information segments comprising a first information segment. For instance, if the statement information inputted by a user is that "my nose is bunged up", the statement information can be divided into two information segments, "my" and "nose is bunged up", or three information segments, "my", "nose" and "bunged up", wherein "nose is bunged up" or "bunged up" can serve as the first information segment. To be specific, in the embodiment of the present disclosure, the acquired statement information can be divided into a plurality of information segments according to part of speech by means of a natural language processing algorithm.

In addition, after the data processor 103 divides the statement information into a plurality of information segments, the Gaussian embedder 104 can establish the Gaussian distribution of each of the information segments, namely, each of the information segments can be expressed as a Gaussian distribution. The similarity calculator 105 can calculate the similarity between the first information segment and words in a database by means of a similarity model, and the output module 106 can obtain at least one second information segment for describing the first information segment. Wherein the database 101 comprises medical terms, to be specific, it can comprise at least one of medical literature, medical knowledge base and electronic medical records. After the second information segment is acquired, the output module 106 can generate a medical statement that is close to the inputted statement on the basis of the second information segment. The diagnostic system can also output corresponding information according to the generated second information segment or the generated medical statement.

Through the above configuration, a professional term that is close to the inputted statement can be obtained, for example, it can be obtained that the term that is close to "nose is bunged up" is "nasal obstruction", in such a way to quickly and accurately provide a medical term that is close to the inputted statement, and eliminate the differences between medical terms and colloquial expressions.

In an embodiment, the Gaussian embedder 104 can be configured to express an initial Gaussian distribution of each of the information segments by a random initial vector and a random initial matrix, wherein the initial vector and the initial matrix are respectively an expected value vector and a covariance matrix of the initial Gaussian distribution. The Gaussian embedder 104 can also be configured to solve a covariance and an expected value of the Gaussian distribution of each of the information segments by minimizing a target function, and establish the Gaussian distribution of each of the information segments based on the calculated covariance and expected value.

The above operations will be described in detail. Firstly, the use of the signs will be explained. Let w be an information segment, and c(w), refers to the i-th information segment in the context of w. Each information segment w can be expressed as a multi-dimensional Gaussian distribution $N(u_w, \Sigma_w)$, wherein u and $\Sigma$ respectively indicates an expected value vector and a covariance matrix of the multi-dimensional Gaussian distribution, the words of which are embedded by the Gaussian embedder. To simplify the model and calculation, $\Sigma$ can be set as a diagonal matrix. Thus, it is required to solve an expected value and a covariance of the multi-dimensional Gaussian distribution corresponding to each of the information segments. In an embodiment, the solving a covariance and an expected value of the Gaussian distribution of each of the information segments by minimizing a target function can comprise: iteratively solving a target function by means of a random gradient descent algorithm so as to calculate a covariance and an expected value of the Gaussian distribution of each of the information segments, wherein the target function is expressed as follows:

$$L(w, c_p, c_n) = \max(0, 1 - S_1(w, c_p) + S_1(w, c_n));$$

Wherein w is information of an information segment, $c_p$ is an information segment in the context of w in a statement, $c_n$ is a word not in the context of w in a statement, the function $S_1(w, c_n)$ is a similarity function between w and $c_n$, $S_1(w, c_p)$ is a similarity function between w and $c_p$, and max( ) is a maximum function.

The meaning of minimizing the target function lies in that the similarity between the information segment in the context of w and w is higher at least than the similarity between the word not in the context of w and w.

In an embodiment, the iteratively solving a target function by means of a random gradient descent algorithm can further comprise iterating the following processes until a predetermined condition is met:

solving a partial derivative of the target function with respect to an expected value vector and a covariance matrix:

$$\frac{\partial L}{\partial u_{w1}} = -\sum\nolimits_{w1}^{-1}(u_{w1} - u_{w2})$$

$$\frac{\partial L}{\partial \Sigma_{w1}} = \frac{1}{2}\left(\sum\nolimits_{w1}^{-1}\sum\nolimits_{w2}\sum\nolimits_{w1}^{-1} + \left(\sum\nolimits_{w1}^{-1}(u_{w1} - u_{w2})\right)\left(\sum\nolimits_{w1}^{-1}(u_{w1} - u_{w2})\right)^T - \sum\nolimits_{w1}^{-1}\right)$$

wherein $\Sigma$ is a covariance of the Gaussian distribution of an information segment, u is an expectation of the Gaussian distribution of an information segment, and $w_1$ and $w_2$ are two information segments;

updating the expected value vector and the covariance matrix according to the partial derivatives.

In order to obtain the target function, the present disclosure also defines the similarity function, which is expressed as:

$$S_1(w_1, w_2) = \int N\left(x; u_{w_1}, \sum\nolimits_{w_1}\right) \log \frac{N\left(x; u_{w_2}, \sum\nolimits_{w_2}\right)}{N\left(x; u_{w_1}, \sum\nolimits_{w_1}\right)} dx$$

$$= \frac{1}{2}\left\{ tr\left(\sum\nolimits_{w_1}^{-1} \sum\nolimits_{w_2}\right) + (u_{w_1} - u_{w_2})^T \right.$$

$$\left. \sum\nolimits_{w_1}^{-1} (u_{w_1} - u_{w_2}) - \log \frac{\det(\sum\nolimits_{w_2})}{\det(\sum\nolimits_{w_1})} - d \right\}$$

Wherein tr( ) means solving a trace of a matrix, $\Sigma^{-1}$ means the inverse of a matrix, det means solving the value of a determinant, and d is a constant independent of u and $\Sigma$. On the basis of the above definitions and expressions, the present disclosure solves u and $\Sigma$ by means of a random gradient descent algorithm, and $w_1$ and $w_2$ are two information segments.

By means of the similarity function, the target function of each information segment, as well as its expected value and the covariance when the target function is minimized, can be obtained, and therefore the Gaussian distribution of the corresponding information segment can be obtained, In addition, the similarity calculator 105 can be configured to establish a similarity model according to the calculated first information segment, and the covariance and the expected value of the Gaussian distribution of the words in the database; and calculate the similarity between the first information segment and the words in the database.

In an embodiment, the similarity model is expressed as $$S(w_1, w_2) = \int N\left(x; u_{w_1}, \sum\nolimits_{w_1}\right) \log \frac{N\left(x; u_{w_2}, \sum\nolimits_{w_2}\right)}{N\left(x; u_{w_1}, \sum\nolimits_{w_1}\right)} dx$$

$$= \frac{1}{2}\left\{ tr\left(\sum\nolimits_{w_1}^{-1} \sum\nolimits_{w_2}\right) + (u_{w_1} - u_{w_2})^T \right.$$

$$\left. \sum\nolimits_{w_1}^{-1} (u_{w_1} - u_{w_2}) - \log \frac{\det(\sum\nolimits_{w_2})}{\det(\sum\nolimits_{w_1})} - d \right\}$$

wherein, d is a constant, u is the expectation, $\Sigma$ is the covariance, $w_1$ and $w_2$ are two information segments.

The similarity calculator 105 can be configured to sort the words in the database according to the similarity between the words in the database and the first information segment. When acquiring the words close to the first information segment by the above configuration, the words in the database can be sorted and then outputted according to the similarity.

It can be understood that the similarity model $S(w_1,w_2)$ for calculating similarity of the two information segments $w_1$ and $w_2$ can be the same as, or different from, the similarity function $S_1(w_1,w_2)$ for solving the Gaussian distribution of an information segment, because they represent the similarity of two information segments in different solving processes. Where the two similarity functions are the same, the calculated similarity between the information segments is more precise. In the similarity model $S(w_1,w_2)$, the two information segments $w_1$ and $w_2$ used for comparing the similarities respectively represent the acquired information segment inputted by a user and the information segment in the database; and when solving the Gaussian distribution of the information segment, the two information segments $w_1$ and $w_2$ used for comparing the similarities respectively represent the information segment for which the Gaussian distribution is to be solved, and an information segment in the context of the information segment in a statement or an information segment not in the context of the information segment in a statement.

The output module 106 can be configured to obtain a predetermined number of words having the highest similarity based on the sorting of similarity between the words in the database 101 and the first information segment; and use the predetermined number of words as the second information segment.

In the above embodiment, the number of close medical terms to be acquired, namely, the predetermined number, can be set beforehand, and the corresponding number of medical terms (words) can be outputted according to the predetermined number after obtaining the similarity between the first information segment and other words. Thus, at least one medical term that is close to the inputted statement can be acquired, which can help a user inquire information on a disease by using of the medical term.

On this basis, the above embodiment can also further output information on, e.g., the corresponding department, treatment or medication of a disease according to the acquired medical term to provide a better user-friendly experience.

It should be noted that the above medical term processing system can be configured to carry out the data processing method of the present disclosure. Thus, all the operations, steps and features described in relation to the data processing method can be used in the medical term processing system, which also can be used for the data processing method. But for the sake of brevity, some features are only described in one of the medical term processing system and the data processing method. However, those skilled in the art can understand that these features can be combined and incorporated into any of the two methods.

Figure 6:
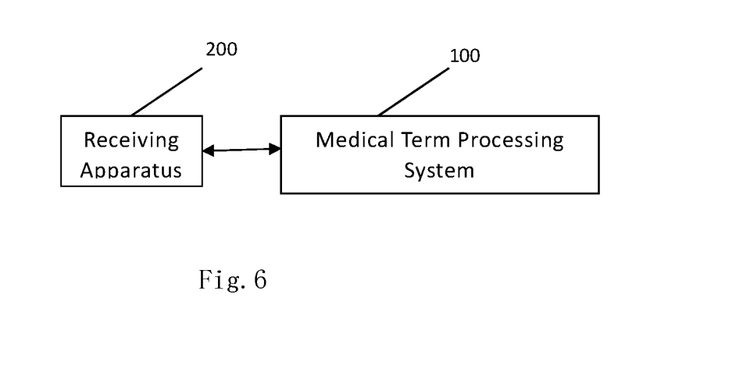
FIG. 6 is a structural block diagram of a medical diagnostic system according to an embodiment of the present disclosure.

According to a further aspect of the present disclosure, there is also provided a medical diagnostic system. As shown in FIG. 6, the medical diagnostic system includes a medical term processing system 100 as described in the above embodiment and a receiving apparatus 200, wherein the receiving apparatus 200 receives the statement information on disease features inputted by a user.

The medical term processing system 100 can divide the statement information into a plurality of information segments, the plurality of information segments comprising a first information segment, and output at least one second information for describing the first information segment. The relevant configuration of the medical term processing system is described in the above embodiment, and will not be reiterated herein.

The receiving apparatus 200 can be configured to receive the statement information inputted by a user. It can receive the statement information by cable communication or wireless communication, or directly receive the statement information by an input apparatus. Meanwhile the statement information can be voice information or text information. The receiving apparatus 200 can convert voice information into text information for subsequent processing.

According to another aspect of the present disclosure, there is also provided a medical intelligent triage apparatus, comprising one or more processors; and a memory storing computer executable instructions configured to perform any method as stated above when executed by the one or more processors.

According to another aspect of the present disclosure, there is also provided a computer readable storage medium, comprising computer executable instructions that cause one or more processors to perform any method as stated above when executed by the one or more processors.

Through the above configuration of the present disclosure, it is possible to provide a medical term that is close to the inputted sentence quickly and accurately, and solve the problem of difference between medical terms and colloquial expressions.

It can be understood that the above depictions are merely exemplary embodiments of the present invention, but the protection scope of the present invention is not limited thereto. It shall be noted that without departing from the spirit and principle of the present invention, those ordinarily skilled in the art can conceive of various modifications or variations, which shall fall within the protection scope of the present invention. Thus, the protection scope of the present invention shall be based on the protection scope of the appended claims.

What needs to be explained is that the above embodiments are only illustrated by way of the individual function modules division. In actual application, the above functions can be allocated to different functional modules as desired. The internal structure of the device can be divided into different functional modules so as to accomplish all or part of the functions as stated above. In addition, function(s) of the above one module can be achieved by a plurality of modules, and functions of the plurality of modules can be integrated into one module.

The present application uses such wordings as "first" and "second". Unless specified in the context, such wordings do not imply any order, but are actually used for the purpose of identification. For instance, the phrases "first information segment" and "second information segment" do not necessarily mean the first information segment is positioned in front of the second information segment, or is generated, received or processed earlier than the second information segment. In fact, these phrases are only used to identify different information segments.

In the claims, any reference sign in parentheses should not be interpreted as a limitation to the claims. The terms "comprise/include" do not exclude the presence of elements or steps other than those listed in the claims. The word "a" or "an" in front of elements does not exclude the presence of a plurality of such elements. The present invention can be realized by hardware comprising several separate elements, or suitably programmed software or firmware, or by any combination thereof.

In an apparatus or system claim enumerating several devices, one or more devices can be embodied in the same hardware project. The fact that some measures are recited in mutually different dependent claims does not mean that the combination of those measures cannot be utilized to advantage.

What is claimed is:

1. A data processing method applied in a medical diagnosis system, comprising:
    acquiring a statement inputted by a user;
    dividing the statement into a plurality of segments by means of a predetermined algorithm, the plurality of segments comprising a first segment, each of the plurality of segments comprises at least one word;
    establishing a Gaussian distribution of each of the segments, comprising:
        expressing an initial Gaussian distribution of each of the segments by a random initial vector and a random initial matrix, wherein the initial vector and the initial matrix are respectively an expected value vector and a covariance matrix of the initial Gaussian distribution,
        solving a covariance and an expected value of the Gaussian distribution of each of the segments by minimizing a target function, and
        establishing the Gaussian distribution of each of the segments based on the calculated covariance and expected value;
    calculating the similarity between the first segment and words in a database by means of a similarity model, the database comprising at least one of medical literature, medical knowledge base and electronic medical records; and
    obtaining, from words in the database, at least one second segment comprising at least one word from the words in the database, for describing the first segment based on the calculated similarity, as an aid for medication recommendations or disease diagnosis.

2. The method according to claim 1, wherein the dividing the statement into a plurality of segments by means of a predetermined algorithm comprises:
    dividing the statement into a plurality of segments according to part of speech by means of a natural language processing algorithm.

3. The method according to claim 1, wherein the solving a covariance and an expected value of the Gaussian distribution of each of the segments by minimizing a target function comprises:
    iteratively solving a target function by means of a random gradient descent algorithm so as to calculate a covariance and an expected value of the Gaussian distribution of each of the segments, wherein the target function is expressed as follows:

$$L(w,c_p,c_n)=\max(0,1-S_1(w,c_p)+S_1(w,c_n));$$

wherein w is information of an segment, $c_p$ is an segment in the context of win a statement, $c_n$ is a word not in the context of w in a statement, the function $S_1(w,c_n)$ is a similarity function between w and $c_n$, $S_1(w,c_p)$ is a similarity function between w and $c_p$, and max( ) is a maximum function.

4. The method according to claim 3, wherein the Gaussian distribution is a multi-dimensional Gaussian distribution that is expressed as $N(u_w, \Sigma_w)$,
    wherein $\Sigma_w$ is a covariance of the Gaussian distribution of the information segment w, $u_w$ is an expectation of the Gaussian distribution of the segment w.

5. The method according to claim 4, wherein the iteratively solving a target function by means of a random gradient descent algorithm comprises:
    iterating the following processes until a predetermined condition is met:
    solving a partial derivative of the target function with respect to an expected value vector and a covariance matrix:

$$\frac{\partial L}{\partial u_{w1}} = -\sum\nolimits_{w1}^{-1}(u_{w1}-w_2)$$

$$\frac{\partial L}{\partial \Sigma_{w1}} = \frac{1}{2}\left(\sum\nolimits_{w1}^{-1}\sum\nolimits_{w2}\sum\nolimits_{w1}^{-1}+\left(\sum\nolimits_{w1}^{-1}(u_{w1}-u_{w2})\right)\left(\sum\nolimits_{w1}^{-1}(u_{w1}-u_{w2})\right)^T - \sum\nolimits_{w1}^{-1}\right)$$

wherein Σ a covariance of the Gaussian distribution of an segment, u is an expectation of the Gaussian distribution of an segment, and $w_1$ and $w_2$ are two segments; and updating the expected value vector and the covariance matrix according to the partial derivatives.

6. The method according to claim 1, wherein the calculating the similarity between the first segment and words in a database by means of a similarity model comprises:

establishing a similarity model according to the calculated first segment, and the covariance and the expected value of the Gaussian distribution of the words in the database; and calculating the similarity between the first segment and the words in the database.

7. The method according to claim 6, wherein the similarity model is expressed as $$S(w_1, w_2) = \int N(x; u_{w_1}, \Sigma_{w_1}) \log \frac{N(x; u_{w_2}, \Sigma_{w_2})}{N(x; u_{w_1}, \Sigma_{w_1})} dx$$

$$= \frac{1}{2} \left\{ tr\left(\Sigma_{w_1}^{-1} \Sigma_{w_2}\right) + (u_{w_1} - u_{w_2})^T \Sigma_{w_1}^{-1} (u_{w_1} - u_{w_2}) - \log \frac{\det(\Sigma_{w_2})}{\det(\Sigma_{w_1})} - d \right\}$$

wherein, d is a constant, u is the expectation of the Gaussian distribution of the segment, Σ is the covariance of the Gaussian distribution of the segment, $w_1$ and $w_2$ are two segments, and N is the multi-dimensional Gaussian distribution in the form of matrix of the segment.

8. The method according to claim 1, wherein the obtaining at least one second segment for describing the first segment comprises:

sorting the words in the database according to the similarity between the words in the database and the first segment so as to obtain a predetermined number of words having the highest similarity; and using the predetermined number of words as the second segment.

9. A medical term processing system using the method according to claim 1, which is applied in a medical information processing system, the medical term processing system comprises:

one or more processors; and a memory storing computer executable instructions configured to perform the following steps when executed by the one or more processors:

dividing a statement input by a user into a plurality of segments by means of a predetermined algorithm, the plurality of segments comprising a first segment, each of the plurality of segments comprises at least one word;

establishing a Gaussian distribution of each of the segments, comprising:

expressing an initial Gaussian distribution of each of the segments by a random initial vector and a random initial matrix, wherein the initial vector and the initial matrix are respectively an expected value vector and a covariance matrix of the initial Gaussian distribution, solving a covariance and an expected value of the Gaussian distribution of each of the segments by minimizing a target function, and establishing the Gaussian distribution of each of the segments based on the calculated covariance and expected value;

calculating the similarity between the first segment and words in a database by means of a similarity model, the database comprising at least one of medical literature, medical knowledge base and electronic medical records; and obtaining, from words in the database, at least one second segment comprising at least one word from the words in the database, for describing the first segment based on the calculated similarity, as an aid for medication recommendations or disease diagnosis.

10. The medical term processing system according to claim 9, wherein the computer executable instructions are configured to divide the statement into a plurality of segments according to part of speech by means of a natural language processing algorithm.

11. The medical term processing system according to claim 9, wherein the computer executable instructions are configured to establish a similarity model according to the calculated first segment and the covariance and the expected value of the Gaussian distribution of the words in the database; calculate the similarity between the first segment and the words in the database; and sort the words in the database according to the similarity between the words in the database and the first segment; and to output a predetermined number of words as the second segment according to the order of the words in the database.

12. The medical term processing system according to claim 9, wherein the solving a covariance and an expected value of the Gaussian distribution of each of the segments by minimizing a target function comprises: iteratively solving a target function by means of a random gradient descent algorithm so as to calculate a covariance and an expected value of the Gaussian distribution of each of the segments, wherein the target function is expressed as follows:

$$L(w, c_p, c_n) = \max(0, 1 - S_1(w, c_p) + S_1(w, c_n));$$

wherein w is information of an segment, $c_p$ is an segment in the context of w in a statement, $c_n$ is a word not in the context of w in a statement, the function $S_1(w, c_n)$ is a similarity function between w and $c_n$, $S_1(w, c_p)$ is a similarity function between w and $c_p$, and max( ) is a maximum function.

13. The medical term processing system according to claim 12, wherein the iteratively solving a target function by means of a random gradient descent algorithm comprises iterating the following processes until a predetermined condition is met:

solving a partial derivative of the target function with respect to an expected value vector and a covariance matrix:

$$\frac{\partial L}{\partial u_{w1}} = -\Sigma_{w1}^{-1}(u_{w1} - w_2)$$

$$\frac{\partial L}{\partial \Sigma_{w1}} = \frac{1}{2}\left(\Sigma_{w1}^{-1} \Sigma_{w2} \Sigma_{w1}^{-1} + \left(\Sigma_{w1}^{-1}(u_{w1} - u_{w2})\right)\left(\Sigma_{w1}^{-1}(u_{w1} - u_{w2})\right)^T - \Sigma_{w1}^{-1}\right)$$

wherein Σ is a covariance of the Gaussian distribution of an segment, u is an expectation of the Gaussian distribution of an segment, and $w_1$ and $w_2$ are two segments; and updating the expected value vector and the covariance matrix according to the partial derivatives.

14. The medical term processing system according to claim 10, wherein the similarity model is expressed as $$S(w_1, w_2) = \int N(x; u_{w_1}, \Sigma_{w_1}) \log \frac{N(x; u_{w_2}, \Sigma_{w_2})}{N(x; u_{w_1}, \Sigma_{w_1})} dx$$

$$= \frac{1}{2} \left\{ tr\left(\Sigma_{w_1}^{-1} \Sigma_{w_2}\right) + (u_{w_1} - u_{w_2})^T \Sigma_{w_1}^{-1} (u_{w_1} - u_{w_2}) - \log \frac{\det(\Sigma_{w_2})}{\det(\Sigma_{w_1})} - d \right\}$$

wherein, d is a constant, u is the expectation, Σ is the covariance, $w_1$ and $w_2$ are two segments.

15. A medical diagnostic system comprising a medical term processing system according to claim 9 and further comprising:

a receiving apparatus for receiving the statement on disease features inputted by a user;

the medical diagnostic system divides the statement into a plurality of segments by using the medical term processing system, the plurality of segments comprising a first segment, and outputs at least one second segment for describing the first segment, each of the plurality of segments comprises at least one word.

16. A non-transitory computer readable storage medium, comprising computer executable instructions that cause one or more processors to perform the method according to claim 1 when executed by the one or more processors.

* * * * *